(12) United States Patent
Elst et al.

(10) Patent No.: US 11,401,230 B2
(45) Date of Patent: Aug. 2, 2022

(54) METHOD OF RECOVERING ORGANIC ACIDS FROM AQUEOUS SOLUTIONS

(71) Applicant: VITO NV, Mol (BE)

(72) Inventors: Kathy Elst, Mol (BE); Helene De Wever, Mol (BE)

(73) Assignee: VITO NV, Mol (BE)

( * ) Notice: Subject to any disclaimer, the term of this patent is extended or adjusted under 35 U.S.C. 154(b) by 0 days.

(21) Appl. No.: 16/640,687

(22) PCT Filed: Aug. 21, 2018

(86) PCT No.: PCT/EP2018/072588
§ 371 (c)(1),
(2) Date: Feb. 20, 2020

(87) PCT Pub. No.: WO2019/038303
PCT Pub. Date: Feb. 28, 2019

(65) Prior Publication Data
US 2020/0354302 A1    Nov. 12, 2020

(30) Foreign Application Priority Data

Aug. 24, 2017    (EP) .................................... 17187734

(51) Int. Cl.
*C07C 51/50*    (2006.01)
(52) U.S. Cl.
CPC ..................... *C07C 51/50* (2013.01)
(58) Field of Classification Search
CPC ....... C07C 51/487; C07C 67/08; C07C 57/13; C07C 69/593; C07C 51/50
See application file for complete search history.

(56) References Cited

U.S. PATENT DOCUMENTS

| 8,357,519 B2 * | 1/2013 | Yang ....................... C12N 9/20 435/135 |
| 2004/0210087 A1 | 10/2004 | Meng et al. |
| 2005/0256337 A1 * | 11/2005 | Verser ................... C07C 51/487 562/508 |

(Continued)

FOREIGN PATENT DOCUMENTS

| EP | 0137749 | * 4/1985 | |
| FR | 1250722 A | 1/1961 | |
| WO | WO-2016131818 A1 * | 8/2016 | ............. C12N 15/52 |

OTHER PUBLICATIONS

Kaur et al. (Development of Reactive Extraction systems for Itaconic acid: A step towards In-situ Product Recovery for Itaconic acid fermantation, pp. 1-154, Published Sep. 22, 2014 (Year: 2014).*

(Continued)

*Primary Examiner* — Yevgeny Valenrod
*Assistant Examiner* — Blaine G Doletski
(74) *Attorney, Agent, or Firm* — Kolitch Romano LLP

(57) ABSTRACT

A method of recovering an organic acid from an aqueous solution may include extracting the organic acid dissolved in the aqueous solution into a water immiscible extraction phase. The water immiscible extraction phase has an extractant for the organic acid. The method may also include separating the extraction phase from the aqueous solution, adding an alcohol to the extraction phase separated from the aqueous solution, and forming an ester from the organic acid and the alcohol.

16 Claims, 4 Drawing Sheets

(56) References Cited

U.S. PATENT DOCUMENTS

2013/0331601 A1* 12/2013 Tirronen .............. B01D 11/0492
560/248

OTHER PUBLICATIONS

Kaur et al. (Development of Reactive Extraction systems for Itaconic acid: A step towards In-situ Product Recovery for Itaconic acid fermentation, pp. 1-154, Published Sep. 22, 2014) (Year: 2014).*
Bankole (Uncatalyzed esterification of biomass-derived carboxylic acids, pp. 1-154, Published 2011) (Year: 2011).*
Kaur et al., "Development of Reactive Extraction systems for Itaconic acid: A step towards In-situ Product Recovery for Itaconic acid fermentation", paper, published Sep. 22, 2014; RSC Advances.
Gordon et al., "Integrated process development of a reactive extraction concept for itaconic acid and application to a real fermentation broth", research article, published Feb. 17, 2017, Engineering in Life Sciences.
European Patent Office, International Search Report and Written Opinion of the International Search Authority of the International Searching Authority, dated Nov. 26, 2018, in PCT/EP2018/072588, which is the international application to this U.S. application.

* cited by examiner

METHOD OF RECOVERING ORGANIC ACIDS FROM AQUEOUS SOLUTIONS

TECHNICAL FIELD

The present disclosure is related to methods of efficiently recovering organic acids, such as carboxylic acids, from aqueous solutions, in particular from fermentation broths.

BACKGROUND

To facilitate the transition towards a biobased economy, research is performed to produce building blocks for bioplastics from renewables. These are often di-acids, such as succinic, itaconic, and 2,5-furan-dicarboxylic acid that are produced by fermentation with first and second generation sugars. In addition, also other acids like citric and lactic acid are currently already produced by fermentative means.

In order to be able to use the acids for instance as a raw material for biobased plastics, these acids have to be recovered and purified. The full process train necessary to achieve the required purity, i.e., the downstream processing, is considered to be the dominant cost and estimated to be around 60% of the production cost. Therefore, continued efforts are made to achieve more efficient processes.

In order to recover these acids from the fermentation broth, several techniques can be applied. Examples are crystallisation/salt-precipitation, electrodialysis and extraction. Salt-precipitation is often applied for the recovery of organic acids (also on an industrial scale for citric and lactic acid), is relatively simple, but requires neutralizing the fermentation broth and is incompatible with an approach to increase the fermentation performance. It also results in a gypsum side stream. Electrodialysis has limitations with regard to the salt composition of the medium, and is generally speaking quite expensive. The limited solubility of the organic acids in non-polar solvents also limits the options of liquid-liquid extraction.

It is known from US 2004/0210087 21 Oct. 2004 (US'087) and US 2005/0256337 17 Nov. 2005 (US'337) to recover carboxylic acids from a solution comprising a salt of the carboxylic acid. In US'087 ammonium or an (water soluble) amine is added to a fermentation broth to form an ammonium salt of the carboxylic acid. The fermentation broth is then heated to split the ammonium salt and produce the acid in the presence of an organic extractant which is immiscible in water, e.g. a tertiary amine. The carboxylic acid is then reacted with an esterifying agent, such as an alcohol. In US'337 the carboxylic acid salt comprises a cation that forms an insoluble carbonate salt, such as Ca, Zn, Ba and Mg. A tertiary amine and $CO_2$ are added to the aqueous salt solution to form an acid-amine complex and the insoluble carbonate salt. The acid-amine complex is recovered from the aqueous salt solution by adding a water immiscible solvent, in particular an alcohol, to form a reaction phase that includes the acid-amine complex and the water immiscible solvent. The reaction phase forms a separate phase from the aqueous solution and is separated. An ester is then formed from the acid and the alcohol solvent.

One disadvantage of both processes is that the fermentation broth is neutralized (by adding ammonium as in US'087 or alkaline earth metal cation as in US'337) which generates a useless end stream following recovery of the acid and also presents an extra unit operation not compatible with an in-situ product recovery approach. Additionally, a salt-splitting reaction is required in both processes, which requires either addition of heat (US'087) or bubbling of $CO_2$ through the fermentation broth which requires extra energy consumption for the reactive extraction step. Furthermore, in US'337 the esterification step is performed with the alcohol used as water immiscible solvent in the reactive extraction step. This is a higher alkyl alcohol, resulting in esters which are more difficult to work with.

From the article Development of reactive extraction systems for itaconic acid: a step towards in situ product recovery for itaconic acid fermentation, K. Elst and G. Kaur, RSC Adv., 2014, 4, 45029-45039, it is known to recover itaconic acid through reactive extraction systems based on amine-diluent combinations. High extraction yields were found for extraction systems including trioctylamine, dioctylamine and N-methyldioctylamine as amine extractants solved in 1-octanol, pentylacetate and methyloctanoate. These systems are able to extract the acid from aqueous solutions into a separate phase, in which the acid is complexed with the amine. The article is however silent as to how the acid can be back extracted from the acid-amine complex.

SUMMARY

It is desirable to provide methods of recovering organic acids from aqueous solutions which have an improved overall efficiency and reduced cost. In particular, it is desirable to provide such methods which include a smaller number of unit operations along the process chain so as to arrive at the desired end product and desired purity level.

It is furthermore desirable to provide methods of recovering organic acids from aqueous solutions which are more energy efficient.

According to a first aspect of the disclosure, there is therefore provided a method of recovering an organic acid from an aqueous solution as set out in the appended claims. The method comprises a first step of extracting the organic acid, which is dissolved in the aqueous solution, into a water immiscible extraction phase. The extraction phase comprises an extractant for the organic acid. The extractant is advantageously an organic extractant, and advantageously is or comprises an organic amine able to complex with the organic acid, in particular a tertiary organic amine. The extractant is advantageously a reactive extractant.

In a second step, the extraction phase is separated from the aqueous solution. The extracting step can be performed in an extraction tank, and the extraction phase can be drawn from the extraction tank. Advantageously, the aqueous solution, which may be at least partially depleted from the organic acid, is recycled. For example, the aqueous solution can be drawn from a fermentation broth, and the depleted aqueous solution can be recycled to the fermentation broth.

The organic acid present in the extraction phase is then reacted with an alcohol to form a corresponding ester. The alcohol is added to the extraction phase following separation of the extraction phase from the aqueous solution. The extraction phase and the alcohol can be mixed and fed to an esterifying reactor.

By combining an acid extraction into a water immiscible phase with esterification, a highly efficient method for recovering the organic acid is obtained. These methods can advantageously be run continuously. Methods as described herein further advantageously allow for recycling obtained side streams, such as recycling the depleted aqueous solution to the fermentation broth, and the side stream obtained from esterification to the extraction phase. Methods as described herein therefore allow for truly in situ recovery of the organic acid with very few unit operations.

Devices for recovering organic acids, in particular acids obtained via fermentation, are described herein as well.

BRIEF DESCRIPTION OF THE DRAWINGS

Aspects of the disclosure will now be described in more detail with reference to the appended drawings, wherein same reference numerals illustrate same features and wherein.

DETAILED DESCRIPTION

The organic acids as referred to in the present description advantageously refer to (water-soluble, or at least water-miscible) carboxylic acids that are formed in aqueous media, such as, though not limited to, fermentation broths. Present methods are advantageously applicable to recovery of dicarboxylic acids. These may be linear, branched-chained, saturated, unsaturated, or substituted. Present methods may as well be applicable to other types of carboxylic acids, such as mono-carboxylic acid or poly-carboxylic acids, in particular tri-carboxylic acids (e.g., citric acid). Representative examples of useful dicarboxylic acids are: succinic acid, fumaric acid, malic acid, maleic acid, glutaconic acid, 2,5-furan dicarboxylic acid, aspartic acid, glucaric acid, glutamic acid, levulinic acid and itaconic acid. Representative examples of useful mono-carboxylic acids are: propionic acid (specifically derivative hydroxypropanoic acid), acetic acid, formic acid, butyric acid (and isobutyric acid), valeric acid (and isovaleric acid), caproic acid (and isocaproic acid), caprylic acid, lactic acid. Methods as described herein may be applicable to derivatives of the above acids.

Figure 1:
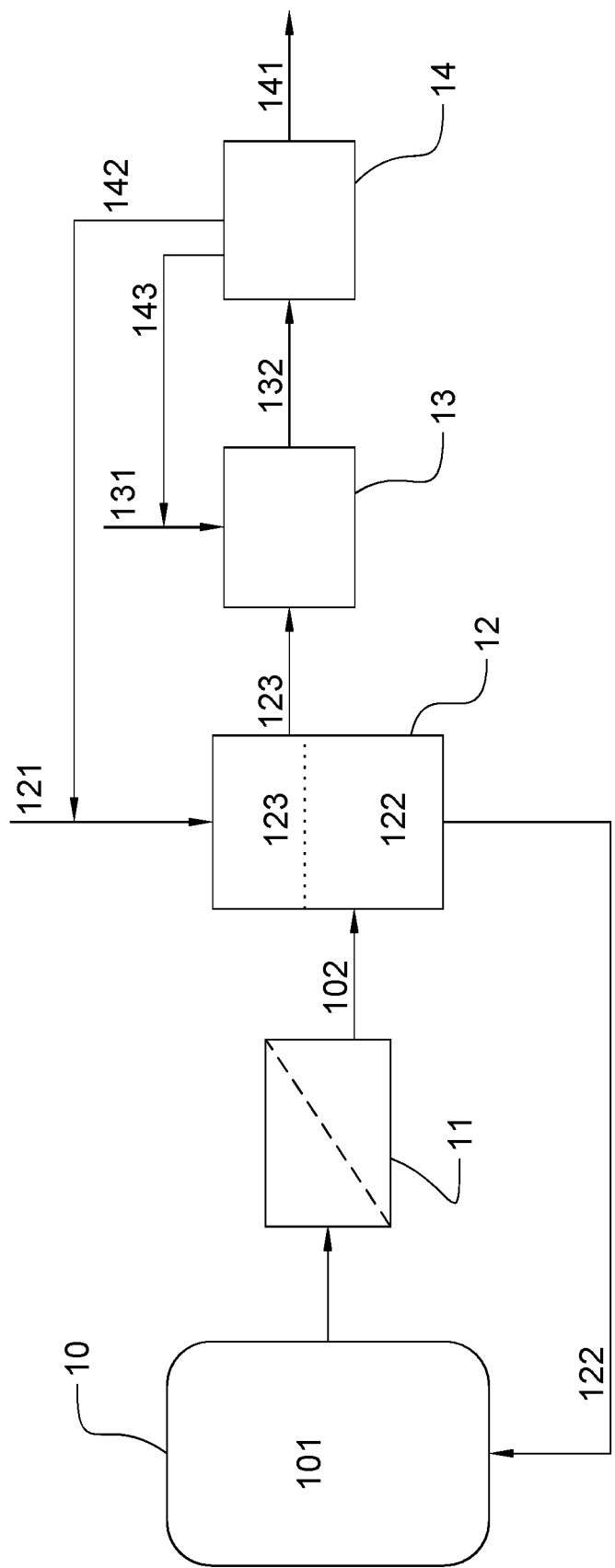
FIG. 1 represents a plant diagram for recovering organic acids from an aqueous solution according to aspects described herein.
Figure 2:
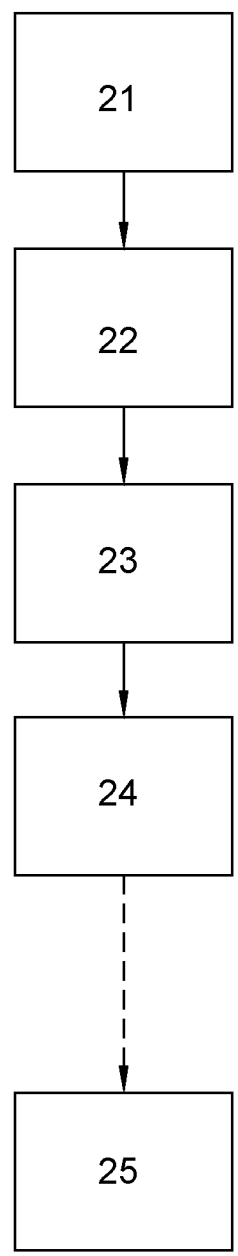
FIG. 2 represents a process flow diagram of methods of recovering organic acids according to aspects as described herein.

The organic acid is advantageously one which is produced through fermentation, in particular fermentation of a sugar in the presence of a microorganism. An enzyme may be used instead of a microorganism. Referring to FIGS. 1 and 2, the fermentation reaction 21 takes place in a fermentation reactor 10 to produce a fermentation broth 101 which contains the organic acid. Suitable microorganisms and sugars for such fermentation reactions are well known to the skilled artisan.

The fermentation reaction 21 typically proceeds at slightly elevated temperatures, such as between 20° C. and 65° C. This is also the temperature at which the fermentation broth 101 is present in reactor 10. The pH of the fermentation broth is preferably acidic, and advantageously between pH 2 and pH 6.5, advantageously between pH 2 and pH 5.5. Nevertheless, also fermentations taking place at neutral pH up to 7.5, e.g. between pH 6.5 and pH 7, or between pH 6.5 and pH 7.5, can be used, provided that the fermentation broth 101 is acidified to acid pH (e.g., pH 6.5 or less) before performing the reactive extraction step.

According to one aspect, the organic acid is recovered from the fermentation broth 101 in an extraction tank 12 in which the extraction step 22 takes place. The fermentation broth is drawn from reactor 10 and supplied to the extraction tank 12. Possibly, a cell retention unit 11 may be arranged between the reactor 10 and the extraction tank 12, which retains microorganisms useful for the fermentation reactions and provides an organic acid feed 102 which is substantially cell-free. Cell retention unit 11 may retain microorganisms by filtration, and therefore comprise or be formed of a filtration unit, such as a microfiltration or ultrafiltration unit. Alternatively, it is possible to use a membrane contactor device as cell retention unit 11. The membrane contactor device may be integrated into extraction tank 12 to fulfil the role of cell separator and extraction at the same time. Feed 102 is supplied to extraction tank 12 and forms an aqueous phase 122 in tank 12. An advantageously organic extractant 121 is added to tank 12. The extraction in tank 12 is advantageously carried out at ambient temperature, or temperatures between 20° C. and 50° C. It may be carried out at substantially a same temperature as the temperature of the fermentation in reactor 10. The extractant is capable of extracting the organic acid from the aqueous phase 122 into an extraction phase 123 which is immiscible with water, and hence is immiscible with phase 122. If desired, the aqueous phase, at least partially depleted from the organic acid, can be recycled to the fermentation reactor 10. The process can be applied in batch or continuously.

As used herein, the term immiscible refers to two compounds or streams forming a two-phase mixture.

Advantageously, unlike the prior art, compounds which would form a salt with the organic acid are not added to feed 102, or reactor 10, nor to extraction tank 12. For example, no ammonia or water miscible amine is added to feed 102. The organic acid is advantageously present in feed 102 in its free form and e.g. not as a salt. It was observed by the inventors that the presence of salts in feed 102 dramatically reduces the extraction yield by amine extractants (trioctyl amine, dioctyl amine) by 10%-20% and more.

One class of useful extractants are reactive extractants which include organic amines, in particular aliphatic amines. The organic amines are advantageously immiscible in water. These are advantageously amines having at least one alkyl-group, wherein each of the at least one alkylgroup comprises at least 6 carbon atoms. The amines also advantageously have boiling points greater than 100° C. (measured at atmospheric pressure) and advantageously at least 175° C. (measured at atmospheric pressure). Primary, secondary, and tertiary amines, as well as quaternary amine salts, can be used. The amines are advantageously tertiary amines, which advantageously have at least six carbon atoms per chain. Among such amines, aliphatic tertiary amines have been found to be most effective.

The nitrogen atom of the amine may be substituted with groups including alkyl, aryl (e.g., phenyl), and aralkyl (e.g., benzyl) groups. These groups, in turn, may be straight chain or branched, and may be substituted or unsubstituted. Examples of substituted groups include halogenated groups (e.g., halogenated alkyl groups) and hydroxyl-containing groups (e.g., hydroxyalkyl groups such as hydroxyethyl and hydroxypropyl). The groups may be the same as, or different from, each other. Alkyl groups are preferred, particularly higher alkyl groups (e.g., having at least 6 carbon atoms, and preferably between 8 and 14 carbon atoms). Examples of useful alkyl amines include trialkyl amines such as trioctyl amine, tridecyl amine, tridodecyl amine, and combinations thereof. Dialkyl amines such as dioctyl amine may be suitable as well.

A second class of useful extractants includes solvating extractants such as carbon bonded oxygen bearing extractants, phosphorus bonded oxygen bearing extractants, phosphine sulfide extractants, and alkyl sulfide extractants. These solvating extractants advantageously have boiling points of at least 175° C. (measured at atmospheric pressure). Specific examples of useful carbon-oxygen extractants include alcohols (e.g., alkyl alcohols having between 8 and 14 carbon atoms, such as octanol, decanol, and dodecanol), ethers (e.g., alkyl ethers such as dibutylcarbitol), ketones (e.g., decanone), and amides (e.g., N,N-dialkyl amides such as N,N-dibutyl formamide, N,N-dibutyl acetamide, N,N-dibutyl propionamide, N,N-dipropyl propionamide, and N,N-di-n-butyl lactamide). Specific examples of useful phosphorus-oxygen extractants include phosphorus esters (e.g., alkyl phosphates such as tri-n-butylphosphate, dibutyl-butylphosphonate, and dimethylmethylphosphonate), and phosphine oxides (e.g., tri-n-octylphosphine oxide). Specific examples of useful phosphine sulfides include tri-isobutylphosphine sulfide. Specific examples of useful alkyl sulfides include dihexyl sulfide and diheptyl sulfide.

Any of the above-described extractants may be used alone or in combination with other extractants, or other compounds. In particular, it may be useful to combine an organic amine extractant with one of the solvating extractants.

A water insoluble, or water immiscible diluent may be added to the tank 12, either together with the extractant 121, or separately. The diluent is miscible with the extractant and advantageously reduces the viscosity of the extraction phase 123 in order to facilitate the extraction of the organic acid from the aqueous phase 122. For example, an alkyl alcohol having at least 6 carbon atoms, and advantageously a total of between 8 and 16 carbon atoms may be combined with the organic amine. The alcohol may facilitate separation of the acid from the fermentation broth. It will however be advantageous to use an ester, an alkane or combinations thereof as diluent instead of an alcohol. As will be described, alcohols may participate in downstream esterification reactions to yield a blend of different types of esters, or non-volatile esters which will be more difficult to separate. Therefore, the diluent—and hence the extraction phase 123—advantageously does not comprise substantial amounts of an alcohol.

Most advantageous are esters used as diluent. For example, an ester having at least 5 carbon atoms, and advantageously a total of between 7 and 16 carbon atoms may be used as diluent and combined with the organic amine. The ester may be linear, or branched-chain, saturated, or substituted. Specific examples of suitable esters are pentyl acetate, methyl octanoate and triglycerides. Alternatively, or in addition, a hydrocarbon may be used as diluent and combined with the organic amine. The hydrocarbon may be linear or aromatic, branched or unbranched. One class of suitable hydrocarbons are alkanes. For example, an alkane having at least 5 carbon atoms, and advantageously a total of between 7 and 16 carbon atoms may be used as diluent and combined with the organic amine. Examples of useful alkanes are hexane, heptane and octane. Toluene can be used as diluent as well. The weight ratio of diluent to extractant in the extraction phase is advantageously less than or equal to 5, advantageously less than or equal to 4, advantageously less than or equal to 2.5, The diluent advantageously forms the largest part of the extraction phase, i.e., weight ratio of at least 1.

As the extraction phase 123 is enriched with the organic acid, e.g. either in dissolved or complexed form, it is separated from the aqueous phase 122 and removed from the tank 12, e.g. by decantation or centrifugation. In the flow chart of FIG. 2, this separation step is indicated by block 23. The extraction tank 12 therefore advantageously comprises a feed inlet for the aqueous solution 102, an inlet for the extractant/diluent 121 and an outlet for the extraction phase 123. The extraction tank may further comprise an outlet for recycling the depleted aqueous phase 122, and which may be fluidly connected to the reactor 10.

The organic acid in the extraction phase 123 is now back extracted to separate the extractant (and possibly the diluent) from the acid in step 24. According to one aspect, the organic acid is back extracted as an ester. The extraction phase 123 is fed to an esterification reactor 13. An esterifying agent 131 is added to reactor 13. The esterifying agent reacts with the organic acid to form the corresponding ester.

Suitable esterifying agents include alcohols, in particular alkyl alcohols. Alcohols having a total of between 1 and 5 carbon atoms are preferred. Specific examples of useful alcohols are methanol and ethanol. These alcohols advantageously provide a fast and efficient reaction, at relatively short residence times. The residence time of the mixture of extraction phase and esterifying agent in reactor 13 is advantageously between 1 min and 240 min, advantageously 120 min or less, advantageously 60 min or less, advantageously 40 min or less. The residence time refers to the average time in which a stream stays inside the reactor. For continuous processes, residence time may be calculated as the volume of reactor divided by the sum of the (volumetric) flow rates of all in-going streams.

During the esterifying reaction, the acid is de-complexed. Advantageously, the extractant and/or the diluent does not react during the esterification reaction, and is retained substantially unmodified in the product stream 132 supplied from reactor 13. The product stream 132 comprises the ester of the organic acid, and advantageously the extractant and possibly the diluent. In order to obtain a single type ester stream, alcohols are advantageously not used as diluent.

The esterification reaction is advantageously catalyst-free, i.e. no catalyst is used, which leaves no catalyst residues in the product, and avoids any undesired reaction of the extractant and/or diluent with the catalyst. A catalyst-free esterification reaction is advantageously less affected by the presence of water that can be formed during esterification.

The extraction phase 123 may comprise small amounts of water, e.g. 5% or less by weight, typically between 0.1% and 3% by weight. In addition, the esterifying reactions may produce additional amounts of water.

Alternatively, the esterification reaction may be catalyzed by a suitable catalyst. The catalyst is advantageously immobilized in the reactor 13. One class of useful catalyst includes heterogeneous catalyst. The catalyst is advantageously an acid functionalised catalyst. Specific examples of useful heterogeneous catalysts are acid grafted mesoporous silicas (such as with sulfonic acids), heteropolyacids, sulfonated mesoporous organic polymers, and aminophosphonic acid resins. Another class of useful catalysts includes enzymes, such as esterase or lipase.

The esterification reaction is advantageously carried out at elevated temperature, such as between 100° C. and 350° C., advantageously between 120° C. and 320° C., advantageously between 150° C. and 300° C. It may be useful to carry out the esterification reaction at elevated pressure, such as pressures of at least 5 bar, advantageously at least 10 bar, advantageously between 20 bar and 250 bar.

Product stream 132 may be fed to a separator 14 to separate the ester 141 from a stream 142 which may include water, the extractant and/or the diluent. Stream 142 may be recycled to the extraction tank 12. Separator 14 may further be configured to separate the ester 141 from any excess alcohol, which may form a second stream 143 and may be recycled to reactor 13. One suitable class of separation processes 25 to recover the ester is distillation, such as though not limited to membrane distillation. Another suitable class of separation processes is pervaporation.

The ester is a useful starting product that can be used for further processing, such as polymerisation. The back extraction of the organic acid as an ester allows for greatly simplifying the downstream processing and recovering the acid through its corresponding ester in a highly efficient way.

Experiment 1

Figure 3:
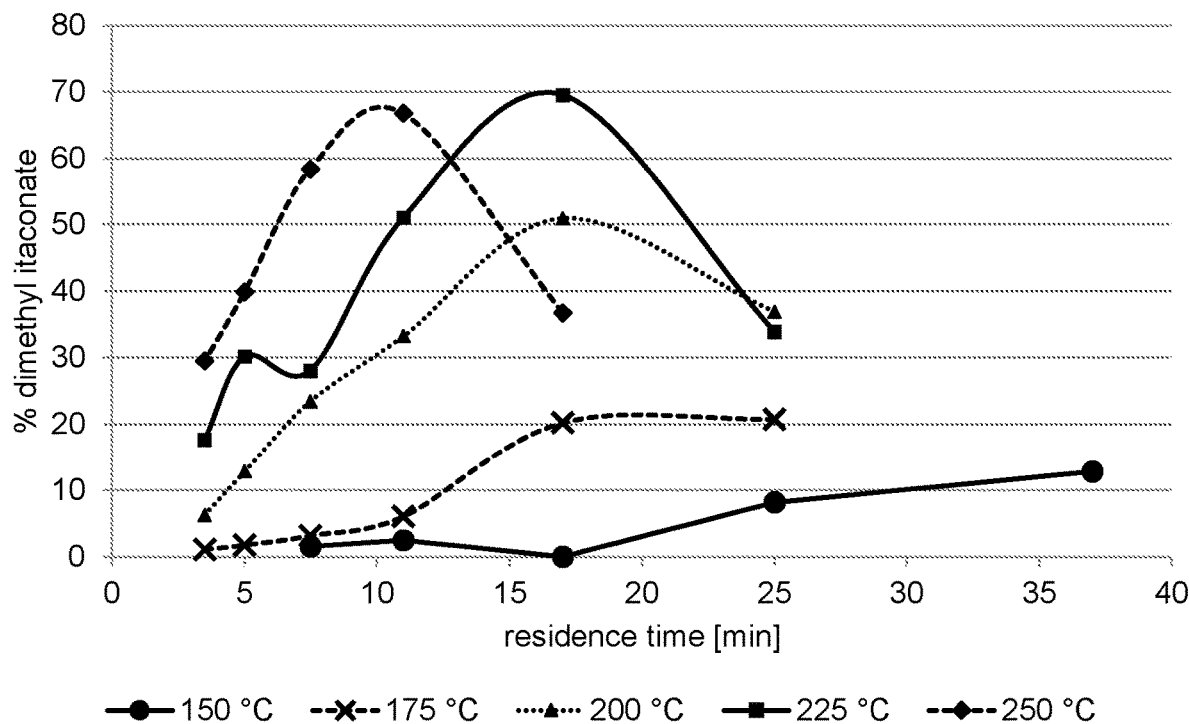
FIG. 3 represents a graph of dimethyl itaconate yield from esterification of itaconic acid according to experiment 1, for different values of residence time in the reactor and for different reaction temperatures at a pressure of 150 bar.
Figure 4:
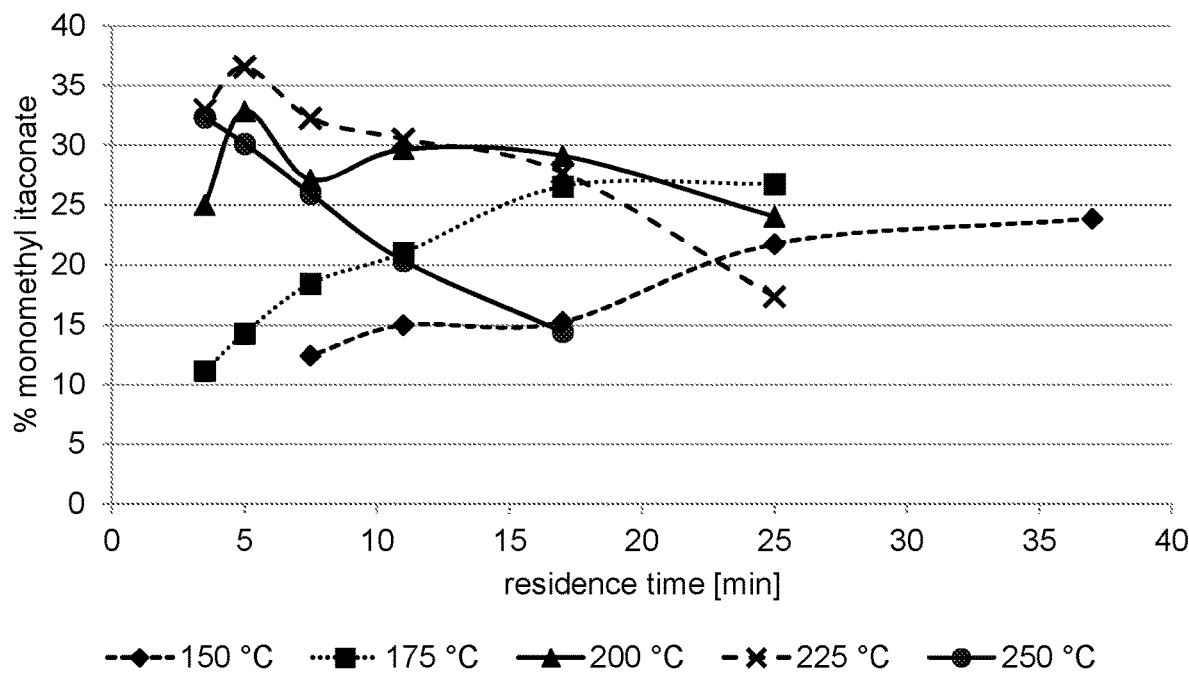
FIG. 4 represents a graph of monomethyl itaconate yield from esterification of itaconic acid according to experiment 1, for different values of residence time in the reactor and for different reaction temperatures at a pressure of 150 bar.

A feed solution was prepared to simulate an extraction phase for itaconic acid, as would result from reactive extraction based on trioctylamine and with methyl octanoate as diluent to show the feasibility of the esterification reactions. The relative amounts of itaconic acid and trioctylamine in the feed solution were 1 mole itaconic acid to 2 moles trioctylamine. The ratio of trioctylamine to the diluent methyl octanoate in the feed solution was 0.4 g/g. The water content of the feed solution was measured and resulted about 1% by weight. The feed solution so obtained was mixed with methanol in a 1 g/g ratio (methanol/feed). This mixture was pumped into a continuous reactor held at a specified temperature. Reaction temperatures between 150° C. and 250° C. were tested. The pumping rate was adjusted to achieve a specified residence time. Residence times between 3 min and 35 min were tested. The reaction pressure was held at 150 bar. Under these conditions an esterification of the complexed mixture was observed as indicated in FIGS. 3 and 4. No catalyst was used. At a temperature between 200° C. and 250° C. up to 70% conversion of itaconic acid into dimethyl itaconate and 30% monomethylitaconate was observed (conversion rates based on the molar ratio of the ester product against the dosed itaconic acid).

Experiment 2

Figure 5:
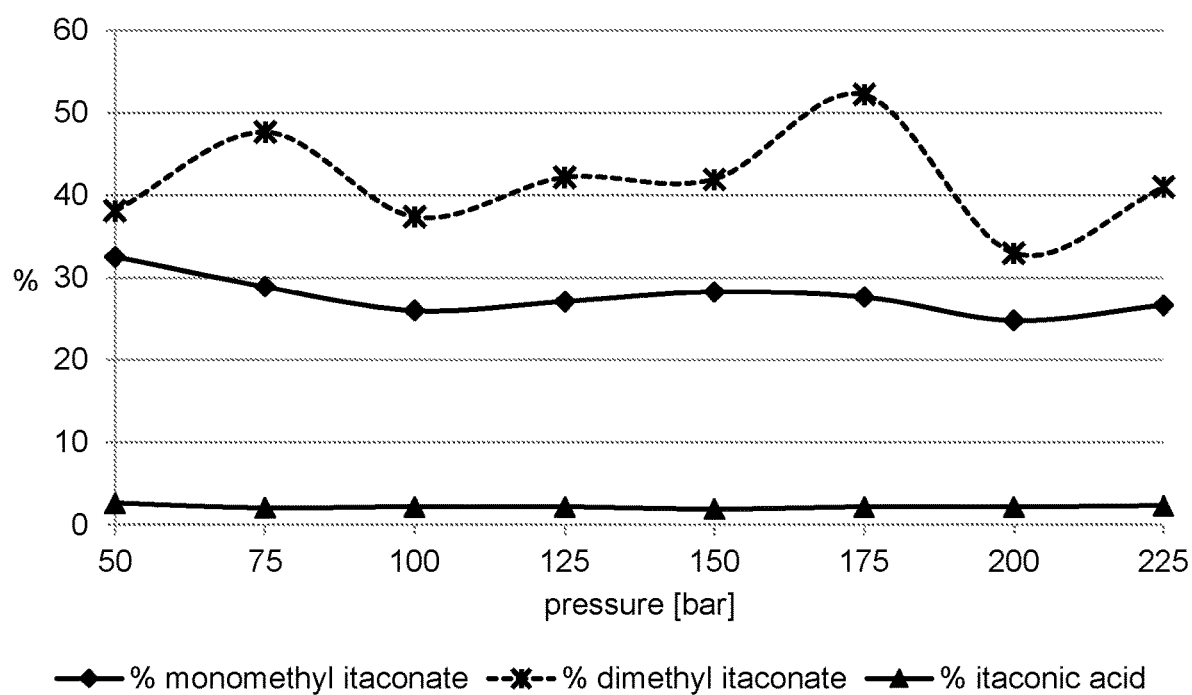
FIG. 5 represents a graph of dimethyl itaconate and monomethyl itaconate yield from esterification of itaconic acid according to experiment 2, for different values of reaction pressure.

A feed solution was prepared following the procedure in experiment 1. The feed solution was mixed with methanol in a 0.5 g/g ratio (methanol/feed). This mixture was pumped into a continuous reactor at 200° C. and the pumping rate was adjusted to obtain a residence time of 17 min. Reaction pressures between 50 bar and 225 bar were tested, as shown in FIG. 5. From FIG. 5 it can be seen that useful conversion rates of the acid into the corresponding ester were obtained for a wide range of reaction pressure, without presence of catalysts. As can also be seen in FIG. 5, the itaconic acid reacted almost completely.

The invention claimed is:

1. A method of recovering an organic acid from a salt: free aqueous solution, the method comprising:
    extracting the organic acid dissolved in the salt-free aqueous solution into a water immiscible extraction phase comprising an extractant for the organic acid, wherein the extractant forms a complex with the organic acid, wherein the extractant is a water immiscible organic amine, wherein the complex is an acid-amine complex formed by the organic amine and the organic acid, and wherein the acid-amine complex is dissolved in the extraction phase;
    adding a water immiscible diluent to the extraction phase, wherein the water immiscible diluent is alcohol-free diluent comprising esters, alkanes, or combinations of esters and alkanes, wherein the diluent forms the largest part of the extraction phase and is miscible with the extractant;
    separating the extraction phase from the salt-free aqueous solution;
    adding an alcohol to the extraction phase separated from the salt-free aqueous solution; and
    reacting the extraction phase separated from the salt-free aqueous solution with the alcohol as a catalyst-free esterification reaction, such that the complex of the extractant and the organic acid is de-complexed, and wherein the de-complexed extractant and the alcohol-free diluent do not participate in the esterification reaction, such that only the de-complexed organic acid reacts with the alcohol to form an ester;
    wherein the alcohol is an alkyl alcohol having a total of between 1 and 5 carbon atoms.

2. The method of claim 1, wherein during the extracting step, the salt-free aqueous solution has a pH between 2 and 5.5.

3. The method of claim 1, wherein the organic amine comprises at least one alkyl group of at least 6 carbon atoms.

4. The method of claim 1, wherein the organic amine is a tertiary amine comprising at least six carbon atoms per chain.

5. The method of claim 1, wherein the diluent is an ester.

6. The method of claim 1, wherein the salt-free aqueous solution is drawn from a fermentation broth, and comprising recycling the salt-free aqueous solution to the fermentation broth following the extracting step.

7. The method of claim 1, wherein the esterification reaction comprises heating the extraction phase separated from the salt-free aqueous solution and the alcohol to a temperature between 100° C. and 350° C.

8. The method of claim 1, wherein the esterification reaction comprises bringing the extraction phase separated from the salt-free aqueous solution and the alcohol to a pressure of at least 5 bar.

9. The method of claim 1, wherein the organic acid is a water soluble dicarboxylic acid.

10. The method of claim 1, further comprising:
    separating the ester from a mixture comprising the extractant; and
    recycling the extractant to the extraction phase.

11. The method of claim 1, wherein the diluent has at least 5 carbon atoms.

12. The method of claim 1, wherein a weight ratio of the diluent to the extractant is from 1 to 5, and wherein the extraction phase comprises 5% or less by weight of water.

13. The method of claim 1, further including separating the ester from a product stream produced by the catalyst-free esterification reaction.

14. The method of claim 1, wherein the catalyst-free esterification reaction produces a single product stream comprising the ester of the organic acid, the extractant, and the alcohol-free diluent.

15. The method of claim 1, wherein the organic amine has an atmospheric pressure boiling point of at least 100° C.

16. A method of recovering an organic acid from a salt-free aqueous solution, the method comprising:

extracting the organic acid dissolved in the salt-free aqueous solution into a water immiscible extraction phase comprising an extractant for the organic acid, wherein the extractant forms a complex with the organic acid, wherein the extractant is a water immiscible organic amine, wherein the complex is an acid-amine complex formed by the organic amine and the organic acid, and wherein the acid-amine complex is dissolved in the extraction phase;

adding a water immiscible diluent to the extraction phase, wherein the water immiscible diluent is alcohol-free diluent comprising an ester, wherein the diluent forms the largest part of the extraction phase and is miscible with the extractant;

separating the extraction phase from the salt-free aqueous solution;

adding an alcohol to the extraction phase separated from the salt-free aqueous solution; and reacting the extraction phase separated from the salt-free aqueous solution with the alcohol as a catalyst-free esterification reaction, such that the complex of the extractant and the organic acid is de-complexed, and wherein the de-complexed extractant and the alcohol-free diluent do not participate in the esterification reaction, such that only the de-complexed organic acid reacts with the alcohol to form an ester;

wherein the alcohol is an alkyl alcohol having a total of between 1 and 5 carbon atoms.

* * * * *